(12) United States Patent
Wills et al.

(10) Patent No.: US 6,720,017 B1
(45) Date of Patent: Apr. 13, 2004

(54) METHOD FOR REDUCING THE RATE OF DETERIORATION OF PERISHABLE HORTICULTURAL PRODUCE

(75) Inventors: Ron Wills, Ourimbah (AU); Ya'Acov Leshem, Rehoboth (IL)

(73) Assignees: Bar-Ilan University, Ramat Gam (IL); The University of Newcastle Research Associates Limited, New South Wales (AU)

( * ) Notice: Subject to any disclaimer, the term of this patent is extended or adjusted under 35 U.S.C. 154(b) by 0 days.

(21) Appl. No.: 09/509,353

(22) PCT Filed: Sep. 23, 1998

(86) PCT No.: PCT/AU98/00799

§ 371 (c)(1),
(2), (4) Date: Jun. 5, 2000

(87) PCT Pub. No.: WO99/15022

PCT Pub. Date: Apr. 1, 1999

(30) Foreign Application Priority Data

Sep. 23, 1997 (AU) .............................. P09370

(51) Int. Cl.[7] ................................. A23L 3/00
(52) U.S. Cl. .................. 426/319; 426/312; 426/615
(58) Field of Search ................................. 426/319, 312, 426/531, 532, 615, 654

(56) References Cited

U.S. PATENT DOCUMENTS 5,128,160 A * 7/1992 Fath et al. .................. 426/316

OTHER PUBLICATIONS

Y.Y. Leshem et al., *Biologica Plantarum*, 38:1–18 (1996).
Y.Y. Leshem, *Plant Growth Reg.*, 18:155–159 (1996).
Y.Y. Leshem et al., *J. Plant Physiol.*, 148:258–263 (1996).
Y.Y. Leshem et al., "NO as a plant growth regulator: interaction with ethylene metabolism," In: *The Biology of Nitric Oxide*, eds. S. Moncada, J. Stamler, S. Gross and E.A. Higgs, Portland Press, London, p. 21 (1996).
Y.Y. Leshem et al., "Chloroplast membrane lipids as possible primary targets for nitric oxide–mediated induction of chlorophyll fluorescence in *Pisum sativum* (argentum mutant)," In: *Physiology, Biochemistry and Molecular Biology of Plant Lipids*, eds. J.P. Williams, M.U. Khan and N.W. Lem. Kluwer Academic Publishers, Dordrecht, pp. 157–159 (1997).
Y.Y. Leshem et al., *Plant Physiol. Biochem.*, 35(7):573–579 (1997).
*The Merck Index*, p. 1041, 1051 (Abstract only), 1989.
*ChemOffice 2001*, Nitric Oxide [10102–43–9], QX025000, X1003257–2.
*ChemOffice 2001*, Nitrous Oxide [10024–97–2], QX1350000, X1003263–0.

* cited by examiner

*Primary Examiner*—Leslie Wong
(74) *Attorney, Agent, or Firm*—Fish & Richardson P.C.

(57) ABSTRACT

A method for reducing the rate of deterioration of perishable horticultural produce by causing the horticultural produce to be treated post harvest with nitric oxide in an amount and for a period of time sufficient to reduce the rate of deterioration of the horticultural produce.

22 Claims, No Drawings

METHOD FOR REDUCING THE RATE OF DETERIORATION OF PERISHABLE HORTICULTURAL PRODUCE

This application is a National stage filing of PCT/US98/00799 filed Sep. 23, 1998.

TECHNICAL FIELD

This invention relates to a method for reducing the rate of deterioration of perishable horticultural produce and in particular relates to the use of nitric oxide (NO) in such a method. More particularly, the horticultural produce to which the method is applicable, is fruit, vegetables and/or flowers. The method is applicable during post-harvest handling, storage and marketing.

BACKGROUND ART

Fresh horticultural produce such as fruit, vegetables and flowers, are highly perishable and degrade rapidly after harvest. This results in substantial quantities of harvested produce being discarded at some point in the postharvest chain or being marketed at a discounted price. The overall outcome is a reduction in the quality of the available food.

There are many causes of deterioration in horticultural produce but an important factor is the accumulation of ethylene in the atmosphere around such produce. It is well known that ethylene accelerates deterioration in horticultural produce. This may be through initiation of premature ripening, acceleration of the loss of green colour, and/or the development of yellowing. It may also result in the increase in microbial growth, induction of physiological disorders and/or the development of undesirable flavours and texture. It may also cause the promotion of leaf petal damage in the case of flowers. Thus, the net effect of ethylene is the enhancement of senescence and rotting of non-climacteric produce and the initiation of ripening of climacteric produce.

Ethylene is generated by all horticultural produce. Thus, it can accumulate to relatively high concentrations in the confined spaces of postharvest containers or storage chambers. Ethylene can also be derived from a wide range of other sources related to the incomplete combustion of fuels as in motor cars, fork lift vehicles or equipment powered by an internal combustion engine. Ethylene can also be derived from the cross contamination with ethylene produced from one commodity accumulating around other commodities held in the same storage chamber.

Traditionally, a threshold concentration of 0.1 $\mu$L/L ethylene was considered to be the safe limit of ethylene exposure. However, recent studies in Australia on a wide range of horticultural produce has shown there is no safe limit of ethylene exposure and that concentrations above 0.005 $\mu$L/L produce a deleterious response. These findings have emphasised the benefit that can be obtained from either preventing the accumulation of ethylene around produce or from inhibiting the action of ethylene that does accumulate around produce.

DISCLOSURE OF THE INVENTION

Nitric oxide has been shown to be metabolised by growing vegetative plants. The application of nitric oxide at low concentrations has also been found to reduce the production of ethylene by young, growing vegetative cells from leaf epidermis and foliar cells and assist in growing plants cope with water stress. Conversely the application of nitric oxide at higher concentrations enhances ethylene production and reduces the ability of growing plants to cope with stress. Prior to now, nitric oxide has not been considered for use on mature plant organs such as fruit, vegetables and flowers.

It has been surprisingly found that nitric oxide can be used to extend the postharvest life of perishable horticultural produce such as fruit, vegetables and/or flowers, by reducing the rate of deterioration of such produce. This is achieved by nitric oxide through a reduction in the rate of rot development, loss of green colour and associated enhancement of yellowing, ripening of fruits, and expression of chilling injury.

It has further been surprisingly found that nitric oxide can inhibit transpiration, that is, evaporation of water from produce. Water comprises 85–95% of the composition of virtually all horticultural produce and after harvest water is continually evaporated into the atmosphere due to humidity differentials. It is important that the loss of water is minimised as it plays a crucial role in the maintenance of appearance and texture in the produce. The loss of about 3% water induces visible changes in produce quality such as wilting and shrivelling. The price paid for wilted and shrivelled produce is thus severely discounted.

The problem of loss of water is important for all produce but is particularly serious for produce such as leafy vegetables and flowers which have a high surface area:volume ratio. Our research has found that the nitric oxide treatment inhibits the rate at which water is evaporated from produce during subsequent storage in air.

Thus, according to this invention there is provided a method for reducing the rate of deterioration of perishable horticultural produce by fumigating said produce, postharvest, with nitric oxide.

Typically, the perishable horticultural produce is fruit, vegetables and/or flowers. Ideally, the nitric oxide should be applied within a few hours after harvest before any undesirable postharvest changes have occurred.

Suitably, the container housing the produce to be treated by the method of this invention is purged with an inert gas such as nitrogen, prior to introduction of the mixture of nitric oxide and inert gas, as nitric oxide is oxidised in the presence of oxygen.

Fumigation of horticultural produce with nitric oxide is only required for a relatively short period. Periods of 1–24 hours with nitric oxide concentrations of 0.1–200 $\mu$L/L have been found to be effective. The application of 5 $\mu$L/L nitric oxide for 2–6 hours is an effective treatment combination for many types of produce while for some produce a 12–24 hr exposure is acceptable. The optimal fumigation treatment, that is, the nitric oxide gas concentration and the time of exposure, can be varied by raising the nitric oxide concentration and reducing the exposure time, or vice versa.

Variation is also dictated by the produce type and length of the subsequent marketing period. The upper time limit for fumigation is determined by the sensitivity of individual produce to be held in an oxygen free atmosphere before excessive anaerobic metabolism leads to undesirable effects.

Nitric oxide fumigation should occur in an atmosphere that is completely free of oxygen as small amounts of oxygen will react with nitric oxide and thereby render it inactive. Typically, nitric oxide is used in conjunction with an inert gas. Nitrogen is the only inert gas that is relevant commercially due to its cost. Other gases such as carbon dioxide and argon are technically acceptable.

However, it has been found that the presence of up to 2% oxygen in the fumigation chamber atmosphere has little degradative effect on nitric oxide if the fumigation time is 2 hours or less. It is also possible to increase the initial concentration of nitric oxide to allow some loss of nitric oxide during fumigation. Concentrations of nitric oxide up to 200 µL/L have been successfully applied.

After fumigation, the produce can be held in a normal air atmosphere. The beneficial effects of the fumigation treatment are retained after the nitric oxide is removed. Horticultural produce can be fumigated at any time after harvest but maximum effectiveness is obtained if it is applied soon after harvest.

The fumigation treatment thus provides an additional advantage of treating fresh horticultural produce soon after harvest and then allowing it to move into the normal postharvest chain without the need for any special storage conditions.

The nitric oxide for use in this invention may be purchased commercially in a cylinder of a mixture of nitric oxide and inert gas, or generated in a sealed chamber containing the produce in an inert atmosphere. There are many methods by which nitric oxide can be generated chemically. One such example of a chemical reaction between an acidified solution of potassium nitrite and potassium iodide. In this instance, two solutions are mixed: Solution A is 0.1M potassium iodide +0.1M sulfuric acid; and Solution B is 50 µM potassium nitrite.

BEST AND OTHER MODES FOR CARRYING OUT THE INVENTION

The following describes one embodiment of the invention which should not be considered limiting on the scope thereof.

Horticultural produce was placed in a vessel, sealed and purged with nitrogen free of any oxygen. A mixture of nitric oxide (in the range of 0.1–200 µL/L) in oxygen-free nitrogen was then introduced and the produce fumigated with this mixture. There are no upper or lower limits to the ratio of produce weight to total volume of the fumigation chamber. The critical issue is that the desired concentration of nitric oxide is maintained throughout the fumigation period. A fumigation time of 2 hours with 5 µL/L nitric oxide was found to be effective for many types of produce but the optimal fumigating conditions for individual types of produce need to be experimentally determined.

EXAMPLE 1

Extension in Post Harvest Life of Some Horticultural Produce Achieved by Fumigation with Nitric Oxide in Nitrogen for 2 Hours The time after fumigation when stored in air for each batch of produce to deteriorate to a quality level that is considered unacceptable for consumers is taken as the storage life. For fruit that are marketed in an unripe condition, the time before ripening occurred was taken as the storage life. The storage life for each produce is then compared with a similar batch of produce that have been held in air only at the same temperature. The change in storage life of the nitric oxide treated produce is determined as a % of that of untreated produce.

| Produce | Fumigation Treatment (NO concentration/ 2 hours) | Temperature | Extension in Post-harvest Life | Cause of Deterioration |
|---|---|---|---|---|
| Strawberries | 5 µL/L | 20° C. | 140% | Rotting |
|  | 1 µL/L | 5° C. | 50% | Rotting |
| Limes | 5 µL/L | 20° C. | 130% | Yellowing |
|  | 50 µL/L | 5° C. | 60% | chilling injury |
| Broccoli | 5 µL/L | 20° C. | 200% | Yellowing |
| Lettuce | 5 µL/L | 20° C. | 30% | Rotting |
| Green bean | 50 µL/L | 20° C. | 40% | Yellowing |
| Mushroom | 5 µL/L | 20° C. | 50% | Rotting |
| Kiwi fruit | 1 µL/L | 20° C. | 20% | Ripening |
| Asian leafy vegetables | 5 µL/L | 20° C. | 50% | Yellowing |
| Geraldton wax flower | 1 µL/L | 20° C. | 80% | Wilting, petal drop |
| Christmas bush | 1 µL/L | 20° C. | 30% | Wilting |

EXAMPLE 2

Reduction in Water Loss of Some Horticultural Produce Achieved by Fumigation with 5 µL/L Nitric Oxide in Nitrogen for 2 Hours All produce were weighed before fumigation and were re-weighed 24 hours after fumigation when stored in air. The loss in weight of the nitric oxide treated produce as is determined as a % of that of untreated produce.

| Produce | Reduction in Water Loss |
|---|---|
| Strawberries | −25% |
| Asian leafy vegetables | −15% |
| Basil | −20% |
| Mushroom | −30% |
| Bell pepper | −10% |
| Gerbera | −15% |
| Chrysanthemum | −15% |

Industrial Application

It should be clear that the present invention will find wide applicability in the vegetable, fruit and flower industries.

We claim:

1. A method of reducing the rate of deterioration of perishable horticultural produce, comprising:
   treating the horticultural produce post harvest with nitric oxide in an amount and for a period of time sufficient to reduce the rate of deterioration of the horticultural produce.

2. The method according to claim 1, comprising causing the nitric oxide to be generated to treat the horticultural produce.

3. The method according to claim 1, comprising causing the nitric oxide to be released to treat the horticultural produce.

4. The method according to claim 1, wherein the horticultural produce is treated with the nitric oxide in an atmosphere that is essentially inert with respect to the nitric oxide.

5. The method according to claim 4, wherein the atmosphere contains 2% oxygen or less.

6. The method according to claim 4, wherein the nitric oxide is present in a concentration of about 0.1 to about 200 µL/L of said atmosphere.

7. The method according to claim 5, wherein the nitric oxide is present in a concentration of about 0.1 to about 200 µL/L said atmosphere.

8. The method according to claim 1, wherein the treatment of the horticultural produce comprises fumigating said produce with the nitric oxide.

9. The method according to claim 8, wherein the horticultural produce is fumigated with the nitric oxide in an atmosphere that is essentially inert with respect to the nitric oxide.

10. The method according to claim 8, wherein the nitric oxide is in a nitric oxide and inert gas mixture.

11. The method according to claim 9, wherein the nitric oxide is present in a concentration of between about 0.1 to about 200 µL/L of said atmosphere.

12. The method according to claim 10, wherein the inert gas mixture contains the nitric oxide in a concentration of between 0.1 to about 200 µL/L of said mixture.

13. The method according to claim 12, wherein the produce is fumigated for a period of time between about 2 to about 6 hours, with a concentration of nitric oxide of about 5 µL/L of said inert gas.

14. The method according to claim 12, wherein the produce is fumigated for a period of time between about 1 to about 24 hours.

15. The method according to claim 12, wherein the inert gas mixture of the nitric oxide and an inert gas selected from nitrogen, carbon dioxide and argon.

16. The method according to claim 8, wherein the horticultural produce is purged with an inert gas prior to the produce being fumigated with the nitric oxide.

17. The method according to claim 1, wherein the horticultural produce comprises one or more of fruit, vegetable and flower.

18. The method according to claim 16, wherein the inert gas is selected from nitrogen, carbon dioxide and argon.

19. A method of reducing the rate of deterioration of a perishable horticultural produce, comprising:

effecting treatment of the horticultural produce post harvest with nitric oxide in an amount and for a period of time sufficient to reduce the rate of deterioration of the horticultural produce.

20. The method according to claim 19, wherein the horticultural produce is treated in an atmosphere that is essentially inert with respect to the nitric oxide.

21. The method according to claim 19, wherein the horticultural produce comprises one or more of a fruit, a vegetable and a flower.

22. The method according to claim 19, wherein the horticultural produce comprises flowers.

\* \* \* \* \*